United States Patent
Yang

(10) Patent No.: US 8,285,490 B2
(45) Date of Patent: Oct. 9, 2012

(54) METHOD AND SYSTEM FOR OBTAINING IMPROVED DATA PERFUSION MEASUREMENTS

(75) Inventor: Qing Yang, North Balwyn (AU)

(73) Assignee: Apollo Medical Imaging Technology Pty Ltd, Melbourne (AU)

( * ) Notice: Subject to any disclaimer, the term of this patent is extended or adjusted under 35 U.S.C. 154(b) by 0 days.

(21) Appl. No.: 12/927,906

(22) Filed: Nov. 29, 2010

(65) Prior Publication Data

US 2011/0118615 A1    May 19, 2011

Related U.S. Application Data

(63) Continuation of application No. 10/523,353, filed on Mar. 7, 2005.

(51) Int. Cl.
*G01N 33/48* (2006.01)
(52) U.S. Cl. .......................................................... 702/19
(58) Field of Classification Search .................... 702/19
See application file for complete search history.

*Primary Examiner* — Jerry Lin

(57) ABSTRACT

A method of deriving blood perfusion indices for a region of interest (ROI) of a subject, comprising the steps of administering a contrast agent to the subject during a dynamic imaging scan, converting signal intensity data from raw images of the scan into contrast agent concentration data, deriving parameters from the contrast agent concentration data using at least one transport function that accounts for delay and dispersion of the contrast agent, and calculating the blood perfusion indices from the derived parameters.

5 Claims, 6 Drawing Sheets

METHOD AND SYSTEM FOR OBTAINING IMPROVED DATA PERFUSION MEASUREMENTS

CROSS-REFERENCE TO RELATED APPLICATIONS

This application is a continuation application to and claims the benefit from U.S. application Ser. No. 10/523,353 filed Mar. 7, 2005, and which is hereby incorporated by reference.

FIELD OF THE INVENTION

This invention relates to a method and system of obtaining improved data in blood perfusion measurements, and more particularly to a method and system of deriving blood perfusion indices for a region of interest of a subject.

BACKGROUND TO THE INVENTION

The process of measuring blood flow within a body of a subject non-invasively is useful in diagnosing and treating the subject. This is particularly the case where a part of a subject or patient, such as a tissue or organ, suffers from ischaemia due for example to a stroke. Determining perfusion indices including the blood flow through such a tissue or organ can provide important information to a physician in order to determine an appropriate treatment regime for the patient.

A number of systems pertaining to blood flow information have been disclosed. In general, the systems involve a contrast agent delivered as an intravascular bolus during a dynamic imaging session such as computerized tomography (CT), nuclear medicine (NM) or magnetic resonance imaging (MRI). The temporal profile of the image intensity in a pixel or region of interest (ROI) reflects the characteristics of the contrast agent hence the blood passing through the vasculature. The typical method of obtaining quantitative perfusion indices involves several steps including: (a) convert the signal intensity profile to the contrast concentration profile depending on the type of imaging modality; (b) measure the arterial input function (AIF) from a feeding vessel to the tissue of interest; (c) measure the tissue profile; (d) extract the tissue impulse residue function (IRF) from the AIF and tissue profile using deconvolution; (e) calculate quantitative perfusion indices including blood flow (BF), blood volume (BV) and mean transit time (MTT) using the IRF. Furthermore, the tissue IRF contains information about the flow heterogeneity associated with dispersion of blood transit time through capillaries, which is an important factor determining the efficacy of oxygen delivery to tissue. However, in the case of major vessel disease, such as acute stroke or carotid artery stenosis, the measured AIF is often associated with a delay and dispersion before it reaches the tissue of interest, and causing overestimation of the MTT and underestimation of the BF.

In U.S. Pat. No. 5,190,744 a contrast agent is injected into a patient for the purpose of detecting blood flow abnormalities. This disclosure describes in some detail the different types of agents that can be used and the administration of those agents into the patient. However results of the perfusion process may not be evaluated until some time after the initial injection of the contrast agent and is thus not a real time process. Furthermore there is no disclosure of obtaining quantitative data relating to blood flow and blood volume which can assist a physician to make a relatively quick and accurate diagnosis and decide on what steps can be taken to treat the patient. More particularly this document does not account for any delay or dispersion of the contrast agent in an initial bolus injection.

In U.S. Pat. No. 6,542,769 there is disclosed an imaging system associated with MRI whereby a bolus containing optical and MRI contrast agents is administered to a patient in order to determine perfusion indices. It uses an optical contrast agent which is injected into the patient and is used to define the arterial input function. The optical contrast is injected so as to overcome the problem of the signal intensity of the vasculature not being proportional to the amount of contrast agent with MRI. A disadvantage of measuring the signal change in arteries using MRI is that it does not provide a true indication of the contrast volume as MRI depends upon electromagnetic fields that are altered due to the contrast agent. By using an optical contrast agent the invention disclosed in this document tries to overcome these disadvantages. Again there is no taking into the account the delay and dispersion associated with the bolus progressing through the artery selected and through the tissue or organ in the region of interest.

The present invention seeks to substantially overcome, or at least ameliorate, any one or more of the abovementioned disadvantages.

SUMMARY OF THE INVENTION

According to a first aspect of the invention there is provided a method of deriving blood perfusion indices for a region of interest (ROI) of a subject, the method comprising the steps of:

administering a contrast agent to the subject during a dynamic imaging scan:

converting signal intensity data from raw images of the scan into contrast agent concentration data;

deriving parameters from the contrast agent concentration data using at least one transport function that accounts for delay and dispersion of the contrast agent; and calculating the blood perfusion indices from the derived parameters.

The transport function may represent a probability distribution function of transit times of the contrast agent through the subject. More particularly, the method may further comprise using a first model to represent an arterial transport function $h_a(t)$ through a vessel leading to the ROI, and using a second model to represent a tissue transport function $h_s(t)$ through the ROI. The transport function preferably accounts for the delay and dispersion of the contrast agent simultaneously.

The method may further comprise selecting an arterial input function $AIF_a(t)$ in the vessel, preferably an artery, leading to the ROI by searching pixels taken of the contrast agent concentration data.

The method may further comprise measuring the contrast agent concentration $C(t)$ remaining in the ROI.

The method may further comprise representing $h_a(t)$ using a gamma-variate function (GVF) in the first model such that:

$$h_a(t) = \begin{cases} \dfrac{1}{A_1}(t-t_1)^{\alpha_1} e^{-(t-t_1)/\sigma_1} & (t \geq t_1) \\ 0 & (t < t_1) \end{cases}$$

where $$A_1 = \sigma_1^{1+\alpha_1}\Gamma(1+\alpha_1), \quad \Gamma(\alpha) \equiv \int_0^\infty x^{\alpha-1}e^{-x}\,dx$$

is the Gamma function, $t_1$ is the time taken for the contrast agent to move from the initial measurement of $AIF_a(t)$ to a vessel, preferably an artery, at the entry to the ROI, $\sigma_1$ and $\alpha_1$ are related to the mean transit time and dispersion of $h_a(t)$.

The method may further comprise estimating $h_a(t)$ after deriving values for parameters $t_1$ and $\sigma_1$ and setting $\alpha_1=0$ through the equation:

$$h_a(t) = \begin{cases} \dfrac{1}{\sigma_1}e^{-(t-t_1)/\sigma_1} & (t \geq t_1) \\ 0 & (t < t_1) \end{cases}$$

The method may further comprise determining an estimate for the arterial input function $AIF_t(t)$ of the vessel at the entry to the ROI through the equation:

$$AIF_t(t) = AIF_a(t) \otimes h_a(t) \equiv \int_0^t AIF_a(\tau)h_a(t-\tau)\,d\tau$$

The method may further comprise determining an estimate of blood flow $F_t$ and an estimate of the tissue IRF $R_e(t)$ from the deconvolution of:

$$C(t) = (F_t/k_H)AIF_t(t) \otimes R_e(t)$$

where $k_H = (1-H_a)/(1-H_t)$ is a correction constant taking into account different values of arterial hematocrit $H_a$ and tissue hematocrit $H_t$, since the contrast agent remains in the extracellular fraction of blood (plasma). The hematocrit is the volume fraction of cells in the blood, which has a typical value of $H_a \approx 0.45$ for large vessels such as the artery and a value of $H_t \approx 0.25$ for small vessels such capillaries in tissue.

The method may further comprise determining an estimate for the tissue transport function $h_e(t)$ from the estimated $R_e(t)$ using:

$$h_e(t) = -\frac{d}{dt}R_e(t)$$

The method may further comprise determining a rise time and a mean transit time of $h_e(t)$ in order to determine values of parameters $\alpha_2$ and $\sigma_2$ by assuming $t_2=0$, or determining a peak height and a mean transit time of $h_e(t)$ in order to determine values of parameters $\sigma_2$ and $t_2$ by assuming $\alpha_2=0$, where $\alpha_2$, $\sigma_2$ and $t_2$ are parameters related to the mean transit time and dispersion of $h_e(t)$.

The method may further comprise representing a simulated transport function $h_s(t)$ using a GVF in the second model such that:

$$h_s(t) = \begin{cases} \dfrac{1}{A_2}(t-t_2)^{\alpha_2}e^{-(t-t_2)/\sigma_2} & (t \geq t_2) \\ 0 & (t < t_2) \end{cases}$$

where $A_2 = \sigma_2^{1+\alpha_2}\Gamma(1+\alpha_2)$, $t_2$, $\sigma_2$ and $\alpha_2$ are parameters related to the mean transit time and dispersion of $h_s(t)$ through the ROI.

The method may further comprise estimating $h_s(t)$ using the derived values for parameters $\alpha_2$ and $\sigma_2$ by setting $t_2=0$ through the equation:

$$h_s(t) = \frac{1}{A_2}t^{\alpha_2}e^{-t/\sigma_2} \quad (t \geq 0)$$

or using the derived values for parameters $\sigma_2$ and $t_2$ by setting $\alpha_2=0$ through the equation:

$$h_s(t) = \begin{cases} \dfrac{1}{\sigma_2}e^{-(t-t_2)/\sigma_2} & (t \geq t_2) \\ 0 & (t < t_2) \end{cases}$$

The method may further comprise determining a simulated tissue IRF $R_s(t)$ by:

$$R_s(t) = 1 - \int_0^t h_s(\tau)\,d\tau$$

The method may further comprise determining a simulated contrast agent concentration $C_s(t)$ as:

$$C_s(t) = (F_t/k_H)AIF_t(t) \otimes R_s(t)$$

The method may further comprise fitting the simulated $C_s(t)$ to $C(t)$ using a least squares method according to:

$$S = \sum_t (C(t) - C_s(t))^2$$

The method may further comprise the step of optimising the parameters $F_t$, $t_1$, $\sigma_1$, $\alpha_1$, $\alpha_2$, $\sigma_2$ and $t_2$ by minimizing $S$ iteratively.

The method may further reduce the number of adjustable parameters by fixing $\alpha_1=0$ and $t_2=0$, or fixing $\alpha_1=0$ and $\alpha_2=0$ leading to five adjustable parameters.

The method may further reduce the number of adjustable parameters by fixing a relative dispersion, $\beta_1=\sigma_1/(\sigma_1+t_1)$, of $h_a(t)$ resulting in $\sigma_1$ dependent on $t_1$, hence leading to four adjustable parameters.

The method may further comprise calculating quantitative blood perfusion indices from the optimized parameters of $F_t$, $t_1$, $\alpha_1$, $\alpha_1$, $\sigma_2$, $\alpha_2$ and $t_2$. The perfusion indices may include any one or more of blood flow, blood volume, mean transit time, arterial delay time, arterial dispersion time or relative arterial dispersion, tissue dispersion time or relative tissue dispersion.

Preferably the ROI is a tissue. The ROI may be a pixel or a plurality of pixels in a tissue. The scan may be any one of CT, MRI or NM.

In the brain, many cerebral arteries are small subjecting to partial voluming. The method may further comprise determining a venous input function ($VIF_a(t)$) from a draining vein to estimate an $AIF_a(t)$ where a selected artery has partial voluming, the vein being larger than the artery.

The method may further comprise the step of determining the profile of a venous input function ($VIF_a(t)$) from a large draining vein. The $AIF_a(t)$ may then be scaled up to have the same first-pass bolus peak area as the $VIF_a(t)$ to minimize partial voluming (PV) effect from the $AIF_a(t)$. The first-pass $AIF_a(t)$ and $VIF_a(t)$ profiles can be obtained by fitting the profiles to gamma-variate function (GVF) profiles respectively to remove contrast recirculation effects.

The method may further comprise determining a simulated tissue IRF $R_s(t)$ in the case that the contrast agent does not always remain in the vascular system, such as in a tumour in the subject in order to determine blood perfusion indices and permeability indices using:

$$R_s(t) = 1 - \int_0^t h_s(\tau)\,d\tau + Ee^{-kt}\int_0^t h_s(\tau)e^{k\tau}\,d\tau$$

where $$h_s(t) = \begin{cases} \frac{1}{A_2}(t-t_2)^{\alpha_2}e^{-(t-t_2)/\sigma_2} & (t \geq t_2) \\ 0 & (t < t_2); \end{cases}$$

E is the extraction fraction of the tracer in the blood stream that leaks out of the vessel into tissue, and the tracer clearance rate constant $k=E*F_t/V_e$ is a rate constant at which the leaked contrast agent diffuses back into the blood stream and leaves the tissue, $V_e$ is volume fraction of the extravascular and extracellular space (EES). The permeability surface area product PS can be determined by $PS=-F_t \ln(1-E)$.

The method may further comprise the step of repeating the entire process (except for selecting the AIF and/or VIF) on a pixel-by-pixel basis to produce quantitative maps of the perfusion indices for further analysis and presentation.

According to a second aspect of the invention there is provided computer program means for deriving blood perfusion indices for a region of interest (ROI) of a subject by directing a processor to:

retrieve raw image data from a dynamic imaging scan of the subject after a contrast agent is administered to the subject;

convert signal intensity data included in the retrieved raw image data into contrast agent concentration data;

derive parameters from the contrast agent concentration data using at least one transport function that accounts for delay and dispersion of the contrast agent; and calculate the blood perfusion indices from the derived parameters.

The computer program means may further direct the processor to select an arterial input function $AIF_a(t)$ in the vessel, preferably an artery, leading to the ROI by searching pixels taken of the contrast agent concentration data. An optimal $AIF_a(t)$ may be selected on the basis of early arrival and high and narrow peak for the arterial input function.

The program means may further direct the processor to measure the contrast agent concentration C(t) remaining in the ROI.

The program means may further direct the processor to estimate the arterial transport function through a vessel leading to the ROI, $h_a(t)$, using a GVF in a first model such that:

$$h_a(t) = \begin{cases} \frac{1}{A_1}(t-t_1)^{\alpha_1}e^{-(t-t_1)/\sigma_1} & (t \geq t_1) \\ 0 & (t < t_1) \end{cases}$$

and thereafter estimating $h_a(t)$ after deriving values for parameters $t_1$ and $\sigma_1$ and setting $\alpha_1=0$ through the equation:

$$h_a(t) = \begin{cases} \frac{1}{\sigma_1}e^{-(t-t_1)/\sigma_1} & (t \geq t_1) \\ 0 & (t < t_1) \end{cases}$$

The program means may further direct the processor to determine an estimate for the arterial input function $AIF_t(t)$ of the vessel at the entry to the ROI through the equation:

$$AIF_t(t)=AIF_a(t) \otimes h_a(t)$$

where $\otimes$ is the convolution operator.

The program means may further direct the processor to determine an estimate of blood flow $F_t$ and an estimate of the tissue IRF $R_e(t)$ from the deconvolution of:

$$C(t)=(F_t/k_H)AIF_t(t) \otimes R_e(t)$$

where $k_H=(1-H_a)/(1-H_t)$ is a correction constant taking into account different values of arterial hematocrit $H_a$ and tissue hematocrit $H_t$ since the contrast agent remains in the extracellular fraction of blood (plasma). The hematocrit is the volume fraction of cells in the blood, which has a typical value of $H_a \approx 0.45$ for large vessels such as the artery and a value of $H_t \approx 0.25$ for small vessels such capillaries in tissue.

The program means may further direct the processor to determine an estimate for the tissue transport function $h_e(t)$ from the estimate $R_e(t)$ using:

$$h_e(t) = -\frac{d}{dt}R_e(t)$$

The program means may further direct the processor to determine a rise time and a mean transit time of $h_e(t)$ in order to determine values for parameters $\alpha_2$ and $\sigma_2$ by assuming $t_2=0$, or to determine a peak height and a mean transit time of $h_e(t)$ in order to determine values for parameters $\sigma_2$ and $t_2$ by assuming $\alpha_2=0$, relating to mean transit time and dispersion of $h_e(t)$.

The program means may further direct the processor to estimate a simulated transport function $h_s(t)$ using a GVF in a second model such that:

$$h_s(t) = \begin{cases} \frac{1}{A_2}(t-t_2)^{\alpha_2}e^{-(t-t_2)/\sigma_2} & (t \geq t_2) \\ 0 & (t < t_2) \end{cases}$$

where $A_2=\sigma_2^{1+\alpha_2}\Gamma(1+\alpha_2)$, $t_2$, $\sigma_2$ and $\alpha_2$ are parameters related to the mean transit time and dispersion of $h_s(t)$ through the ROI. Thereafter the program means may direct the processor to estimate $h_s(t)$ using the derived values for $\alpha_2$ and $\sigma_2$ by setting $t_2=0$ through the equation:

$$h_s(t) = \frac{1}{A_2}t^{\alpha_2}e^{-t/\sigma_2} \quad (t \geq 0)$$

or using the derived values for $\sigma_2$ and $t_2$ by setting $\alpha_2=0$ through the equation:

$$h_s(t) = \begin{cases} \frac{1}{\sigma_2} e^{-(t-t_2)/\sigma_2} & (t \geq t_2) \\ 0 & (t < t_2) \end{cases}$$

The program means may further direct the processor to determine a simulated tissue IRF $R_s(t)$ by $$R_s(t) = 1 - \int_0^t h_s(\tau) d\tau$$

The program means may further direct the processor to determine a simulated contrast agent concentration $C_s(t)$ as:

$$C_s(t) = (F_t/k_H) \text{AIF}_i(t) \otimes R_s(t)$$

The program means may further direct the processor to fit the simulated $C_s(t)$ to $C(t)$ using a least squares method according to:

$$S = \sum_t (C(t) - C_s(t))^2$$

The program means may further direct the processor to optimize the values $F_t$, $t_1$, $\sigma_1$, $\alpha_1$, $\sigma_2$, $\alpha_2$ and $t_2$ by minimizing S iteratively.

The program means may direct the processor to reduce the number of adjustable parameters by fixing $\alpha_1 = 0$ and $t_2 = 0$, or fixing $\alpha_1 = 0$ and $\alpha_2 = 0$ leading to five adjustable parameters.

The program means may direct the processor to further reduce the number of adjustable parameters by fixing a relative dispersion, $\beta_1 = \sigma_1/(\sigma_1 + t_1)$, of $h_a(t)$ resulting in $\sigma_1$ dependent on $t_1$, hence leading to four adjustable parameters.

The program means may further direct the processor to calculate quantitative blood perfusion indices from the optimized values of parameters $F_1$, $t_1$, $\sigma_1$, $\alpha_1$, $\sigma_2$, $\alpha_2$ and $t_2$. The perfusion indices may include any one or more of blood flow, blood volume, mean transit time, arterial delay time, arterial dispersion time or relative arterial dispersion, tissue dispersion time or relative tissue dispersion.

Preferably the ROI is a tissue. The ROI may be a pixel or a plurality of pixels in a tissue. The scan may be any one of CT, MRI or NM.

The program means may further direct the processor to determine a venous input function (VIFa(t)) from a draining vein to estimate an AIFa(t) where a selected artery has partial voluming, the vein being larger than the artery.

The program means may further direct the processor to determine the profile of a venous input function (VIF$_a$(t)) from a large draining vein. The AIF$_a$(t) may then be scaled up to have the same first-pass bolus peak area as the VIF$_a$(t) to minimize partial voluming (PV) effect from the AIF$_a$(t). The first-pass AIF$_a$(t) and VIF$_a$(t) profiles can be obtained by fitting the profiles to gamma-variate function (GVF) profiles respectively to remove contrast recirculation effects.

The program means may further direct the processor to determine a simulated tissue IRF $R_s(t)$ in the case that the contrast agent does not always remain in the vascular system, such as in a tumour in a subject in order to determine blood perfusion and permeability indices using:

$$R_s(t) = 1 - \int_0^t h_s(\tau) d\tau + E e^{-kt} \int_0^t h_s(\tau) e^{k\tau} d\tau$$

where $$h(t) = \begin{cases} \frac{1}{A_2} (t-t_2)^{\alpha_2} e^{-(t-t_2)/\sigma_2} & (t \geq t_2) \\ 0 & (t < t_2) \end{cases};$$

E is the extraction fraction of the tracer in the blood stream that leaks out of the vessel into tissue, and the tracer clearance rate constant $k = E^* F_t/V_e$ is a rate constant at which the leaked contrast agent diffuses back into the blood stream and leaves the tissue, $V_e$ is volume fraction of the extravascular and extracellular space (EES). The program means may further direct the processor to calculate the permeability surface area product PS by $PS = -F_t \ln(1-E)$.

The program means may further direct the processor to repeat the entire process (except for selecting the AIF and/or VIF) on a pixel-by-pixel basis to produce quantitative maps of the perfusion indices for further analysis and presentation.

According to a third aspect of the invention there is provided a system of deriving blood perfusion indices for a region of interest (ROI) of a subject, the system comprising:

scanning means for providing a dynamic image scan of the subject during which a contrast agent is administered to the subject;

processor means linked to the scanning means for retrieving raw image data from the scan;

the processor means further:

converting signal intensity data included in the retrieved raw image data into contrast agent concentration data;

deriving parameters from the contrast agent concentration data using at least one transport function that accounts for delay and dispersion of the contrast agent; and calculating the blood perfusion indices from the derived parameters.

BRIEF DESCRIPTION OF THE DRAWINGS

Preferred embodiments of the invention will hereinafter be described, by way of example only, with reference to the drawings wherein.

DETAILED DESCRIPTION OF PREFERRED EMBODIMENTS

Figure 1:
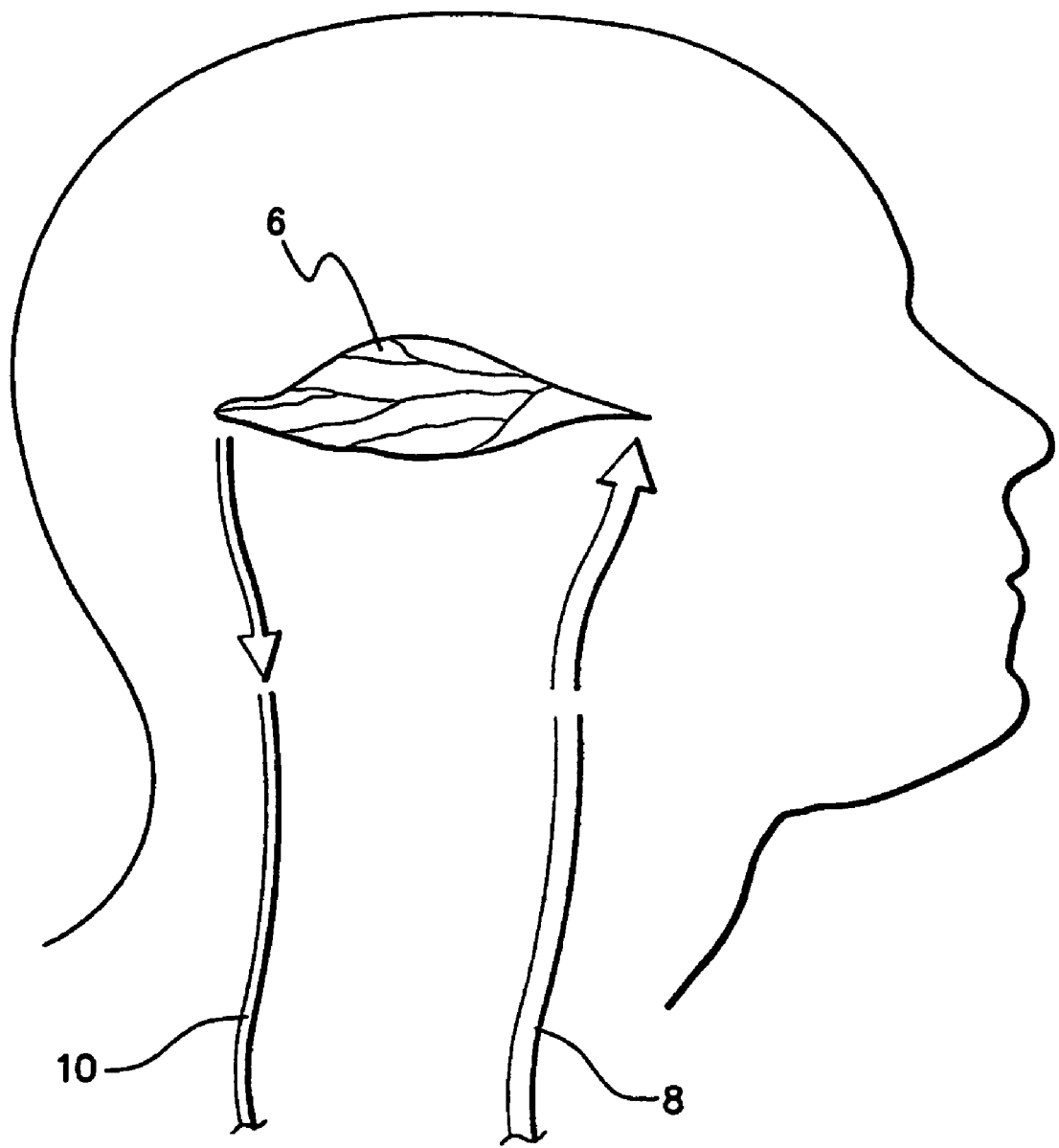
FIG. 1 is a side view of the head of the subject indicating flow of the contrast agent through a region of interest, such as a tissue.
Figure 2:
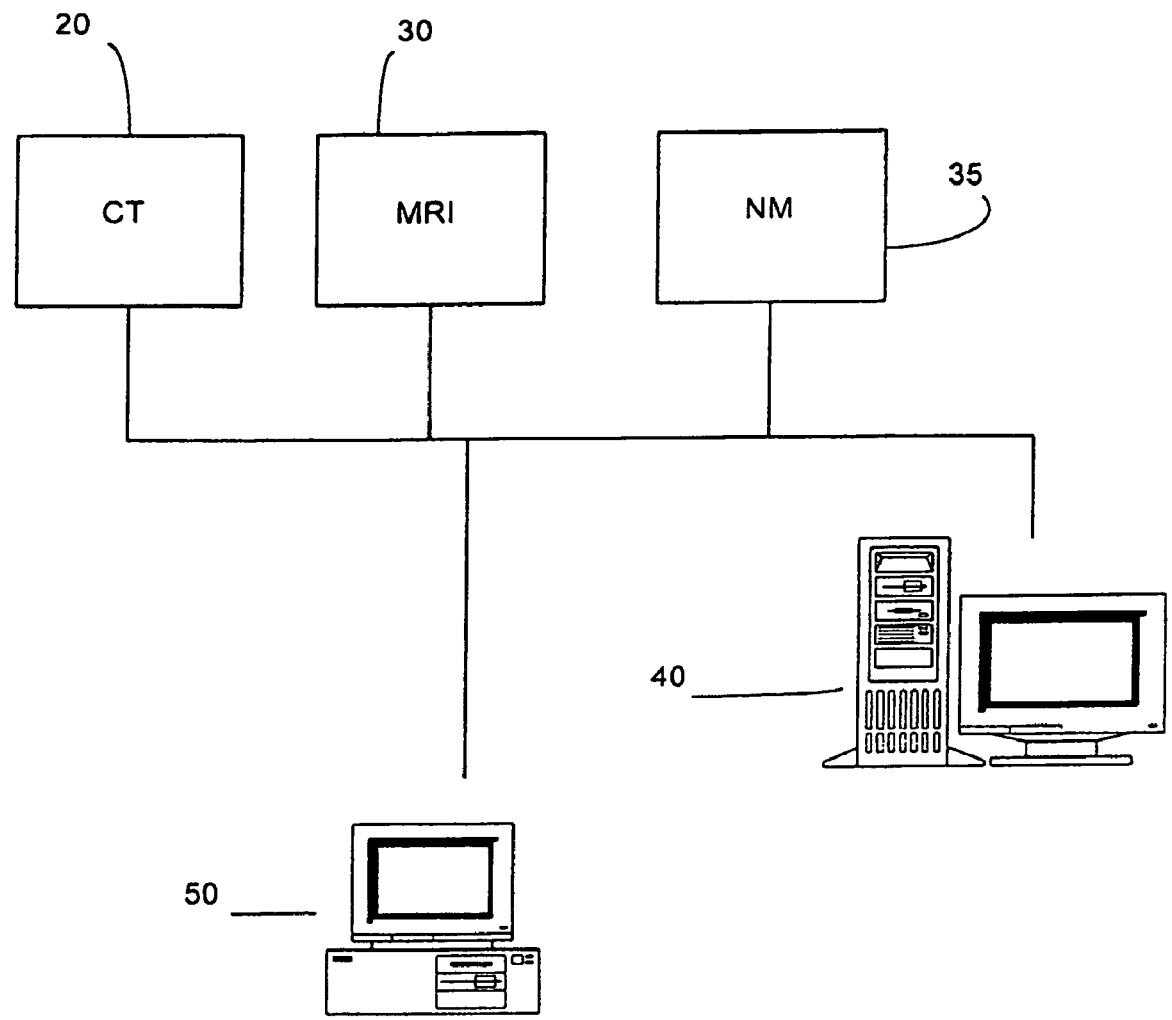
FIG. 2 is a block diagram showing a communications network including a number of scanners linked to a data storage system and a processing system.

The present invention is particularly applicable to CT, MRI and MN imaging systems. A bolus of contrasting agents is introduced via a needle into a patient at, for example, the arm of the patient. However the bolus can be input to any other part of the patient. A region of interest (ROI) may be a tissue 6 in a part of the patient's brain as shown in FIG. 1. Alternatively, the ROI may be a pixel or a plurality of pixels, where many pixels represent a calculated image to produce one or more perfusion maps. Blood circulating throughout the patient will contain the contrast agent and in particular may be delivered to the tissue 6 via artery 8 and the blood flowing through the tissue 6 is returned to the heart via vein 10. Raw data and/or images collected by a scan, such as from a CT scanner 20, MRI scanner 30 or NM scanner 35 are forwarded to a data storage system 40 in the form of a Picture Archiving Communications System (PACS) in FIG. 2. A computer program operating on a processor 50, in the form of a computer, is used to retrieve the various images or raw data from any one of the scanners 20, 30 or 35 or from the data storage system 40. The program then processes those images to provide an improved data set for a clinician to use, particularly in relation to perfusion indices including blood flow, blood volume, mean transit time, arterial delay time, arterial dispersion time or relative arterial dispersion, tissue dispersion time or relative tissue dispersion. The computer program need not reside on computer 50, but may reside in a console computer linked to any one of the scanners 20, 30 or 35. Alternatively the program may reside in a workstation (stand-alone or in a system) or in the PACS 40.

In order to select an appropriate arterial input function, AIF, various images (slices) from a scan are analysed to identify a major artery of interest. In CT the signal changes are directly proportional to the contrast agent concentration profile. However in MRI a mathematical conversion is used in order to convert the measured signal time-curve into contrast agent concentration profile. From the raw data retrieved, the program stored in the memory of system 50 automatically calculates the contrast concentration based on the measured signal intensities of the contrast agent. It then searches all pixels to find the optimal AIF (or VIF) based on the criteria of early arrival, high and narrow peak for AIF, and later arrival, high and broad peak with maximum peak area for VIF. The program displays the searched AIF and VIF pixels on the corresponding images and plots the AIF and VIF time-curves. A user may further select a particular pixel while dynamically viewing its profile against the selected AIF in order to confirm the best arterial input function. A better arterial pixel can be saved to replace or average with the saved AIF and then the user may "click" on further pixels in order to compare the further pixels with the updated AIF until the user is satisfied with the selected AIF. The selection of the best AIF may be done through different slices with the effort to minimize partial voluming (PV) where only a part of the artery is contained in the pixel. Similarly, the best VIF profile can be confirmed by the user.

Figure 5:
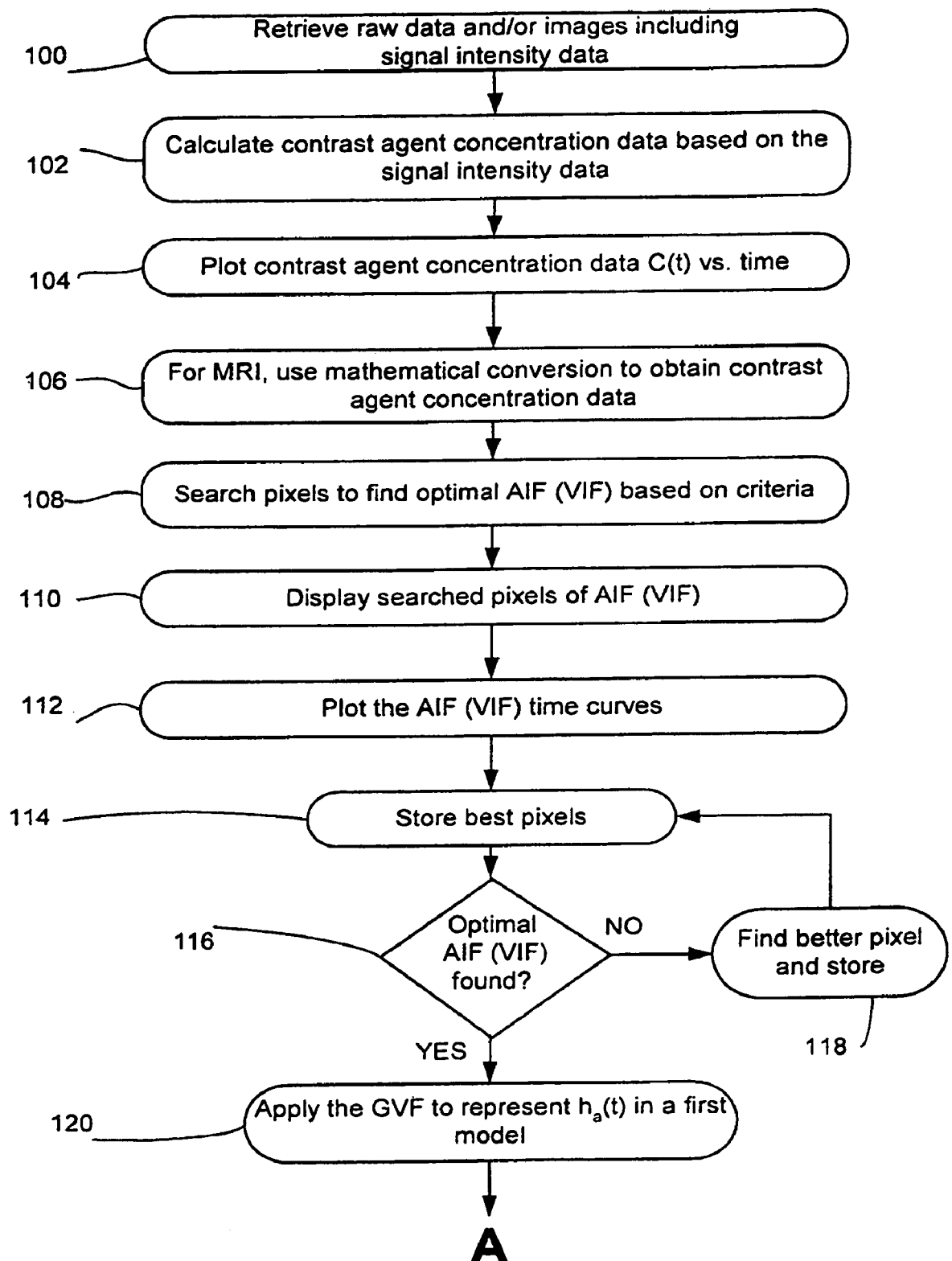
FIG. 5 is a flow diagram showing steps performed by a computer program to obtain values for the blood perfusion indices such as BF, BV and MTT.
Figure 5:
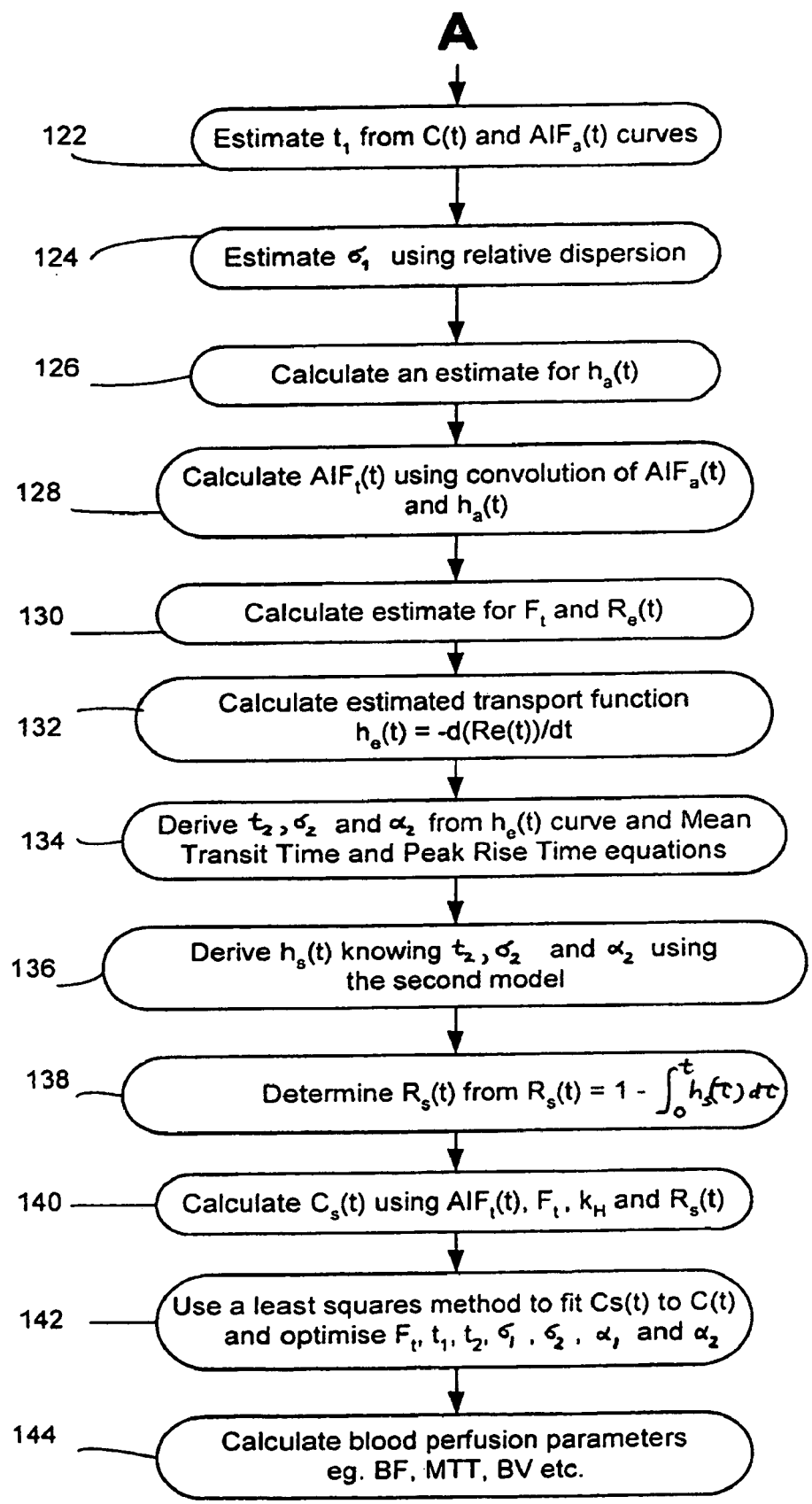

Referring to FIG. 5, the computer program at step 100 thus retrieves raw data and/or images from any one of the scanners 20, 30, 35 or PACS 40, including the signal intensities containing information of the contrast agent. At step 102 the program calculates the contrast agent concentration based on the signal intensities. It then plots the contrast agent concentration profile C(t) against time at step 104. Where the data is retrieved from an MRI scan, the signal intensities are converted mathematically to obtain C(t) at step 106. At step 108 the program searches pixels taken from the plots to find an optimal AIF (VIF) based on given criteria such as arrival times and peaks. At step 110 the program displays the searched pixels of the AIF (VIF) and plots these as a function of time at step 112. The best pixel(s) to date are then stored in memory means, such as located at computer 50, at step 114. A decision is made at step 116 to determine if the optimal pixel has been found and stored, which decision can be made by the user. If an optimal pixel has not been found, the program keeps reverting to step 118 to find a better pixel than the pixel stored, which is subsequently stored at step 114. When an optimal pixel has been found the process moves to step 120, to be described hereinafter.

The amount of contrast agent passing through the tissue 6 may then be measured by the computer program, the contrast agent concentration being represented as C(t).

Thus two known profiles are used by the computer program, one for the concentration of the contrast agent C(t) and the other for $AIF_a(t)$, being the arterial input function in the vessel (artery) leading to the ROI, against time. By knowing these two particular profiles the tissue blood flow $F_t$ and tissue impulse residue function (IRF), R(t), can be derived from a deconvolution of the equation $C(t)=(F_t/k_H) AIF_a(t) \otimes R(t)$, where $k_H=(1-H_a)/(1-H_t)$ is a correction constant taking into account different values of arterial hematocrit $H_a$ and tissue hematocrit $H_t$ since the contrast agent remains in the extracellular fraction of blood (plasma). The hematocrit is the volume fraction of cells in the blood, which has a typical value of $H_a \approx 0.45$ for large vessels such as the artery and a value of $H_t \approx 0.25$ for small vessels such capillaries in tissue.

In other words the concentration of the contrast agent is derived by a convolution of the arterial input function and the tissue IRF multiplied by the tissue blood flow. This is the case where there is no delay or dispersion so that the selected $AIF_a(t)$ from a major artery is taken to be the same as the $AIF_t(t)$ directly feeding the tissue.

Figure 3:
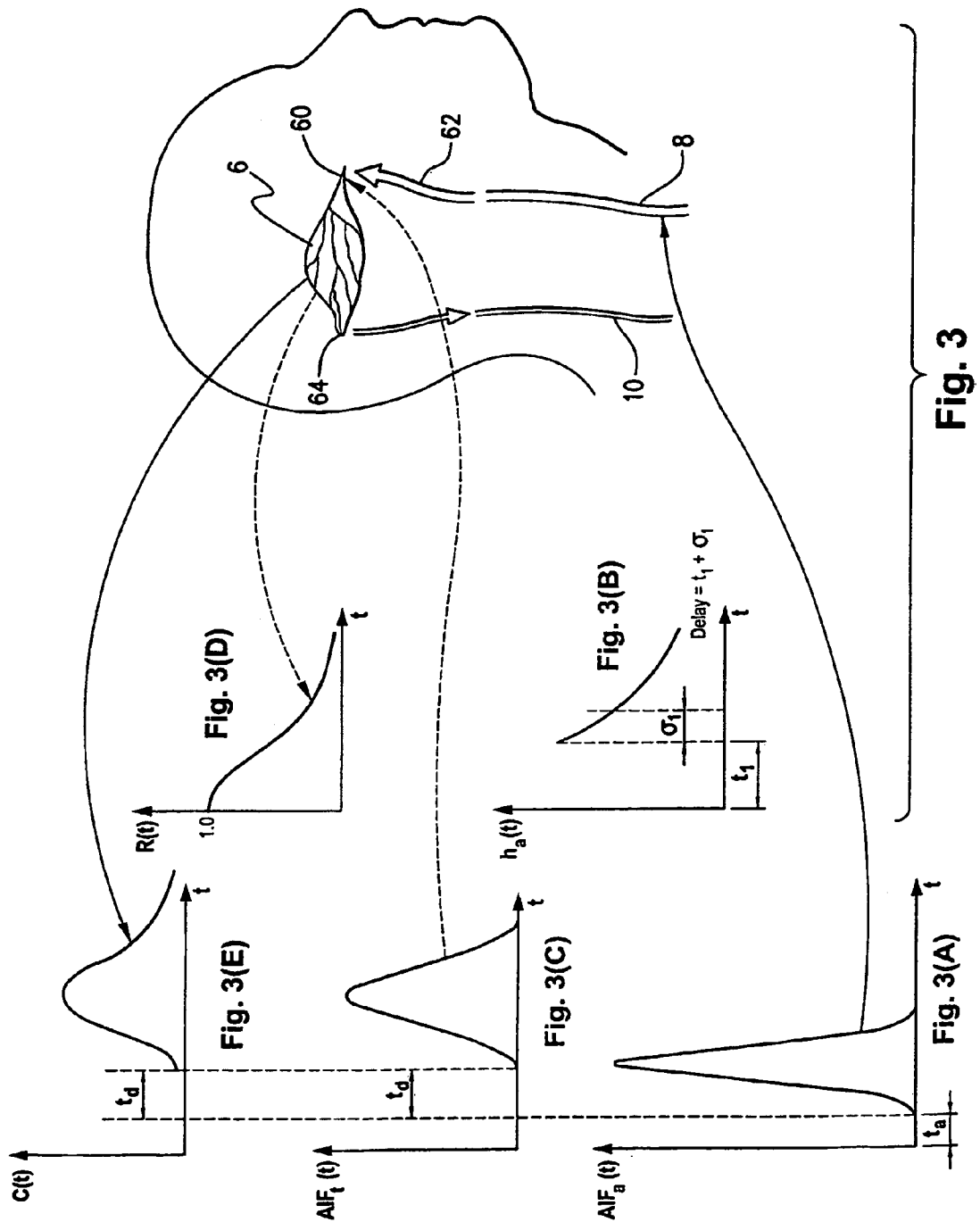
FIG. 3 shows various graphs against time at different parts of the subject's head as the contrast agent traverses the region of interest and the input artery.

In practice however it is difficult to measure the arterial input function at the input to different tissues of interest. This is due to the practicalities that, arteries directly feeding the tissues are usually small in size and subject to a substantial partial voluming effect. In the case of major vessel disease such as acute stroke or carotid artery stenosis, the AIF selected from a major artery is often associated with a delay and dispersion before it reaches the abnormal tissue of interest. As an example reference is made to FIG. 3 where the arterial input function is measured in artery 8 resulting in the graph of FIG. 3(A). It can be seen from the graph that there is a time $t_a$ taken from injection for the contrast agent to arrive at the point where the arterial input function is measured in artery 8. It results in a narrow 'pulse' having a large amplitude. Then in FIG. 3(C) there is shown the arterial input function if measured at the tissue 6 input artery designated by 60. It can be seen that the graph has dispersed somewhat or broadened, as well as involving a time delay $t_d$ in traversing the smaller artery 62 where a vessel disease such as stroke or stenosis may occur. Other normal small arteries supplying different tissues may have little delay and dispersion. Therefore it is practically useful to select a normal large vessel such as the internal carotid artery (ICA), middle cerebral artery (MCA), anterior cerebral artery (ACA) or posterior cerebral artery (PCA) through multiple slices in the head and neck of the patient. The transit of the contrast agent from the artery 8 through the artery or arteries 62 up to the entry point 60 of the tissue 6 is described by the vascular transport model (VTM) using the delay $t_d$ and an estimated dispersion parameter to derive a simulated function $AIF_t(t)$ at the tissue input artery 60. The next part of the transit of the concentration of the contrast agent is described by the tissue perfusion model (TPM) where the contrast agent traverses across the tissue 6 from an input 60 to an output 64. The measured contrast concentration profile C(t) represents the contrast agent remaining in the tissue 6 as represented by the curve shown in FIG. 3(E) and the tissue blood flow $F_t$ and impulse residue function (IRF) $R_e(t)$ can be estimated using a model-free deconvolution technique such as the singular value decomposition (SVD) method. However, such deconvolution is sensitive to noise, which may produce some mathematical solutions of $R_e(t)$ but without any physiological meaning. Further, the estimated $F_t$ and $R_e(t)$ may not be accurate due to uncertainties associated with unaccounted delay and dispersion effects. It is desirable to use a constrained deconvolution process using a model derived IRF $R_s(t)$ with a typical shape as shown in FIG. 3(D). The estimated $R_e(t)$ can be used to derive parameters for $R_s(t)$.

A simulated tissue contrast concentration curve derived using convolution as $C_s(t)=(F_t/k_H)\text{AIF}_t(t) \otimes R_s(t)$ can be fitted to the measured $C(t)$ curve by optimizing the model parameters through an iterative least square method.

The gamma-variate function (GVF), represented by equation (1) below, has been generally used to describe the temporal profile of contrast during blood circulation through the vascular system.

$$GVF = \begin{cases} \frac{1}{A}(t-t_0)^\alpha e^{-(t-t_0)/\sigma} & (t \geq t_0) \\ 0 & (t < t_0) \end{cases} \quad (1)$$

In order to account for the delay and the dispersion through the artery 62 the computer program employs a first model of GVF to represent a vascular transport function as $$h_a(t) = \begin{cases} \frac{1}{A_1}(t-t_1)^{\alpha_1} e^{-(t-t_1)/\sigma_1} & (t \geq t_1) \\ 0 & (t < t_1) \end{cases} \quad (2)$$

Where $$A_1 = \sigma_1^{1+\alpha_1}\Gamma(1+\alpha_1) \text{ since } \int_0^\infty h_a(t)\,dt \equiv 1, \Gamma(\alpha) \equiv \int_0^\infty x^{\alpha-1}e^{-x}\,dx$$

is the Gamma function, $t_1$ is the time taken for the initial $\text{AIF}_a(t)$ measured from artery 8 to arrive at artery 60 and $\sigma_1$ and $\alpha_1$ are related to the mean transit time and dispersion of $h_a(t)$. If setting $\alpha_1=0$, equation (2) becomes, $$h_a(t) = \begin{cases} \frac{1}{\sigma_1} e^{-(t-t_1)/\sigma_1} & (t \geq t_1) \\ 0 & (t < t_1) \end{cases} \quad (3)$$

An example plot of $h_a(t)$ versus time is shown in FIG. 3(B). The value of $t_1$ can be estimated by $t_d$ as the delay between $C(t)$ in FIG. 3(E) and $\text{AIF}_a(t)$ in FIG. 3(A). Starting with an estimate of $\alpha_1=0$, the mean transit time of $h_a(t)$ is $t_1+\sigma_1$ and a relative arterial dispersion is defined as $\beta_1=\sigma_1/(t_1+\sigma_1)$ ranging from 0 to 1. A relative dispersion value of $\beta_1=12\%$ is chosen based on previous measurements of dispersions typical for arteries (12%), vein (30%) and whole organs (40%). Thus an initial estimate of $\sigma_1$ can be obtained as $t_1\beta_1/(1-\beta_1)$.

Referring again to FIG. 5, at step 120 the computer program applies the GVF to represent $h_a(t)$ in a first model. At step 122 an estimate of $t_1$ is made from the plots of $C(t)$ and $\text{AIF}_a(t)$. Then at step 124, the program estimates $\sigma_1$ using $t_1$ and a relative dispersion value $\beta_1$ assuming $\alpha_1=0$. The process then moves to step 126.

With the estimated $t_1$, $\alpha_1$ and $\sigma_1$ values, the estimated $h_a(t)$ function in equation (2) can be calculated by the computer program at step 126 to describe the arterial transport by $$\text{AIF}_t(t) = \text{AIF}_a(t) \otimes h_a(t) \quad (4)$$

where $\text{AIF}_t(t)$ is the arterial input function at the input to the tissue designated by 60, $\text{AIF}_a(t)$ is the initial AIF at artery 8 and $\otimes$ is the convolution operator.

The contrast concentration profile in the tissue of interest can be further determined by $$C(t) = (F_t/k_H)\text{AIF}_t(t) \otimes R_e(t) \quad (5)$$

where $k_H=(1-H_a)/(1-H_t)$ is a correction constant taking into account different values of arterial hematocrit $H_a$ and tissue hematocrit $H_t$ because the contrast agent remains in the extracellular fraction of blood (plasma). The hematocrit is the volume fraction of cells in the blood, which has a typical value of $H_a\approx0.45$ for large vessels such as the artery and a value of $H_t\approx0.25$ for small vessels such capillaries in tissue.

With measured $C(t)$ and the model derived $\text{AIF}_a(t)$, an estimate of $F_t$ and $R_e(t)$ can be obtained using a model-free deconvolution technique such as the singular value decomposition (SVD) method. The deconvolution is very sensitive to noise, which may produce some mathematical solutions of $R_e$ but without any physiological meaning. Further, the estimated $F_t$ and $R_e(t)$ may not be accurate due to uncertainties associated with the initial estimate of $t_1$, $\alpha_1$ and $\sigma_1$ values. It is desirable to use a constrained deconvolution process using a model derived IRF with a typical shape as shown in FIG. 3(D).

Again referring to FIG. 5, the computer program stored in memory of the computer 50 directs the computer at step 128 to calculate an estimate for $\text{AIF}_a(t)$ from the convolution of $\text{AIF}_a(t)$ and $h_a(t)$ in equation (4) and at step 130 to calculate an estimate for $F_t$ and $R_e(t)$ from equation (5).

A more realistic (simulated) profile of the tissue IRF can be provided by the second model of GVF, which describes the tissue transport function as $$h_s(t) = \begin{cases} \frac{1}{A_2}(t-t_2)^{\alpha_2} e^{-(t-t_2)/\sigma_2} & (t \geq t_2) \\ 0 & (t < t_2) \end{cases} \quad (6)$$

Where $A_2=\sigma_2^{1+\alpha_2}\Gamma(1+\alpha_2)$, $t_2$, $\sigma_z$ and $\alpha_2$ are parameters related to the mean transit time and dispersion of $h_s(t)$ through the tissue. If assuming $t_2=0$, equation (6) becomes $$h_s(t) = \frac{1}{A_2} t^{\alpha_2} e^{-t/\sigma_2} \quad (t \geq 0) \quad (7a)$$

Several typical characteristic parameters of $h_s(t)$ are determined as

Peak rise time $(RT)=\sigma_2\alpha_2$

Mean transit time $(MTT)=\sigma_2(1+\alpha_2)$ \quad (7b)

Alternately, if assuming $\alpha_2=0$, equation (6) becomes $$h_s(t) = \begin{cases} \frac{1}{\sigma_2} e^{-(t-t_2)/\sigma_2} & (t \geq t_2) \\ 0 & (t < t_2) \end{cases} \quad (8a)$$

Several characteristic parameters of $h_s(t)$ are determined as

Peak height (PH)=$1/\sigma_2$

Mean transit time (MTT)=$t_2+\sigma_2$ (8b)

The relationship between the tissue IRF R(t) and transport function h(t) is $$R(t) = 1 - \int_0^t h(\tau) d\tau \Rightarrow h(t) = -\frac{dR(t)}{dt} \quad (9)$$

Since h(t) is a probability density function, R(t) is a positive, decreasing function of time with a property of with R(0)=1 as shown in FIG. 3(D).

From the estimated $R_e(t)$ profile deconvolved from equation (5), an estimated transport function $h_e(t)$ can be derived as $h_e(t)=-dR_e(t)/dt$. The peak rise time and mean transit time of $h_e(t)$ can then be calculated and used to estimate $\sigma_2$ and $\alpha_2$ using equation (7b) or to estimate $\sigma_2$ and $t_2$ using equation (8b) respectively.

Knowing the estimates of $\sigma_2$ and $\alpha_2$ with $t_2=0$, or knowing $\sigma_2$ and $t_2$ with $\alpha_2=0$, these are then input to equation (6) to determine a simulated transport function $h_s(t)$. The simulated tissue IRF $R_s(t)$ can then be determined from equation (9) as below:

$$R_s(t) = 1 - \int_0^t h_s(\tau) d\tau \quad (10)$$

Once $R_s(t)$ is determined, then the simulated concentration curve can be determined as follows:

$$C_s(t) = (F_t/k_H)AIF_t(t) \otimes R_s(t) = (F_t/k_H)\int_0^t AIF_t(\tau)R_s(t-\tau)d\tau \quad (11)$$

Using the computer program, the user selects the initial AIF and VIF, the program will automatically derive the $AIF_t$(t) input to the tissue 6 based on the first model and the convolution thereof. Secondly the program will estimate tissue blood flow $F_t$ and IRF $R_e(t)$ and derive parameter values used to build the simulated tissue IRF $R_s(t)$ in the second model. The program further calculates a simulated contrast curve at the tissue of interest. The seven parameters $F_t$, $t_1$, $\sigma_1$, $\alpha_1$, $\sigma_2$, $\alpha_2$ and $t_2$ are optimized through a least squares method in order to fit the simulated $C_s(t)$ to the measured tissue curve C(t). A least squares fit can be represented by a minimization process of the quantity S defined in equation (12) below:

$$S = \sum_t (C(t) - C_s(t))^2 \quad (12)$$

With the optimized seven parameters $F_t$, $t_1$, $\sigma_1$, $\alpha_1$, $\sigma_2$, $\alpha_2$ and $t_2$, several quantitative perfusion indices can be determined as Blood Flow (BF)=$F_t$ Mean Transit Time (MTT)=$t_2+\sigma_2(1+\alpha_2)$ Blood Volume (BV)=BF*MTT Arterial Delay Time (DT)=$t_1+\sigma_1(1+\alpha_1)$ Arterial Dispersion Time (ADT)=$\sigma_1\sqrt{1+\alpha_1}$ Tissue Dispersion Time (TDT)=$\sigma_2\sqrt{1+\alpha_2}$ Relative Arterial Dispersion (RAD)=ADT/DT Relative Tissue Dispersion (RTD)=TDT/MTT (13)

These indices can be determined on a pixel-by-pixel basis to produce quantitative perfusion maps respectively for further analysis and interpretation. This provides more accurate information to a clinician so that the clinician can decide on appropriate therapy for the patient on retrieving the above results or data.

Thus referring again to FIG. 5, at step 132 an estimate of the transport function across the ROI is calculated by the computer program using the equation $$h_e(t) = -\frac{d}{dt}R_e(t).$$

At step 134 the program derives $t_2$, $\sigma_2$ and $\alpha_2$ (with either $\alpha_2=0$ or $t_2=0$) from the $h_e(t)$ curve using the equations (7b) or (8b). At step 136 $h_s(t)$ is derived by the program knowing the values for $t_2$, $\sigma_2$ and $\alpha_2$ using the second model. At step 138 $R_s(t)$ is derived from equation (10) by the program. At step 140 $C_s(t)$ is determined by the program using the estimates for $R_s(t)$, $AIF_t(t)$, $k_H$ and $F_t$. At step 142 a least squares method is used by the program to fit $C_s(t)$ to C(t) and to optimize the parameters $F_t$, $t_1$, $\sigma_1$, $\alpha_1$, $\sigma_2$, $\alpha_2$ and $t_2$ by minimising S in equation (12) iteratively. Finally at step 144 the program calculates values for perfusion indices such as BF, MTT and BV etc using equation (13).

An artery is usually selected in the process of obtaining an arterial input function, however in the brain it is not always easy to obtain a major artery. A smaller artery in the brain may be selected instead leading to partial voluming. To compensate for partial voluming, a vein that is much larger than the artery and is usually easy to identify may be used. The user and/or computer program searches for a large vein which should have minimal partial voluming effect. A smaller artery can be selected and scaled against a vein profile. Thus, a profile of a VIF from a large draining vein is determined. The AIF is then scaled up to have the same first-pass bolus peak area as the VIF to minimise the PV effect from the AIF. The first-pass AIF and VIF profiles can be obtained by fitting them to the GVF profiles respectively to remove contrast recirculation effects. The area under the vein profile should be the same as the arterial profile. However, this approach of using a $VIF_a(t)$ to correct for partial volume effects of $AIF_a(t)$ is not applicable outside the brain as the contrast agent does not always remain within the vascular system during transit through the body. Usually in the body a large artery without partial voluming can be found on the imaging slices.

Figure 4:
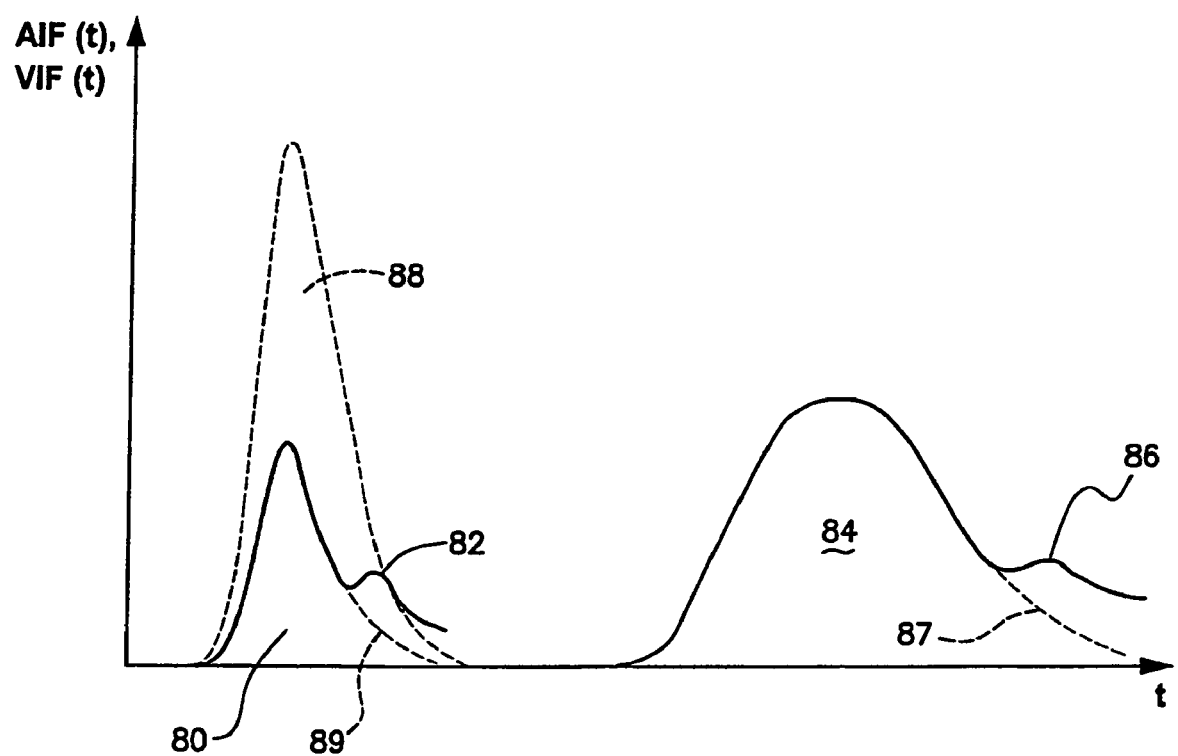
FIG. 4 shows a plot whereby an input arterial profile for a small artery exhibiting partial voluming is scaled up based on a vein profile.

Thus in FIG. 4 the AIF profile 80 of the original artery selected is shown, which is much smaller than the expected profile due to partial voluming. Therefore a vein is selected and it has the VIF profile 84. Due to recirculation effects, each profile shows a local maximum 82 (on the AIF curve) and 86 (on the VIF curve). A GVF is fitted by the computer program to the VIF to obtain an estimate of the total area (BV) under the fitted VIF curve whilst eliminating the local maximum 86 and following contour 87. Then the GVF is applied by the computer program to the selected AIF to eliminate the local maximum 82 and extend the profile along contour 89. The program then uses this estimate to scale up the original AIF 80 to AIF 88 to obtain an estimate of the concentration of contrast agent from the scaled up AIF 88. This approach overcomes the problem when the VIF is represented partly with a missing end portion in the data due to a shorter scanning time in order to keep to a minimum the amount of time a patient has to spent being scanned by a particular scanner.

It is to be noted that the use of a GVF in each of the first and second models is for relative ease of calculations. Should the full GVF be used in both the first and second models, there will be seven adjustable parameters that need to be optimized by the least square fitting process. The computer program may provide various options to allow the user to fix certain parameters such as $\alpha_1=0$ and $t_2=0$ (or $\alpha_1=0$ and $\alpha_2=0$) throughout the least square fitting process, in which only five parameters $F_t$, $\sigma_2$, $\alpha_2$, $\sigma_1$ and $t_1$ (or $F_t$, $\sigma_2$, $t_2$, $\sigma_1$ and $t_1$) would then need to be optimized. The computer program further allows the user to fix the relative arterial dispersion $\beta_1$ thus $\sigma_1$ can be calculated dependent on $t_1$. A fixed value of $\beta_1=12\%$ can be chosen based on previously published results.

Alternately, if one can measure $AIF_t(t)$ by identifying a small artery showing a delay relative to $AIF_a(t)$, optimized $\sigma_1$ and $t_1$ values can be determined by fitting the simulated $AIF_t(t)$ from equations (3) and (4) to the measured $AIF_t(t)$. Then a relative dispersion $\beta_1$ value can be determined and applied to all other pixels of the same subjects assuming a constant relative dispersion. Thus there will be only four parameters $F_t$, $\sigma_2$, $\alpha_2$ and $t_1$ (or $F_t$, $\sigma_2$, $t_2$ and $t_1$) that need to be optimized for increased robustness of the fitting process.

Furthermore, one may apply the above approach to various subjects with vascular abnormalities accompanied by delay and dispersion, such as in acute stroke and stenosis. Once a consistent relative dispersion value $\beta_1$ is determined from all the representing cases, the vascular transport function in equation (3) can be described by a single variable $t_1$ together with a constant $\beta_1$. A two-step method can be implemented to account for delay and dispersion. At first, an initial IRF $R_0(t)$ can be derived by deconvolution of $AIF_a(t)$ from $C(t)$ using the model-free SVD method. The delay time $t_1$ can be determined by the maximum position of $R_0(t)$, i.e. $R_{0max} \equiv R_0(t=t_1)$. The $t_1$ value determined this way is less sensitive to curve noise because the deconvolution involves all data points of the time curve. In the second step, the $AIF_t(t)$ feeding the ROI can be derived from equation (3) with $t_1$ and the constant $\beta_1$, which determine $\sigma_1$. Then value of $F_t$ and corrected IRF $R_e(t)$ can be obtained by deconvolution of the model derived $AIF_t(t)$ from $C(t)$ using the SVD method. Perfusion indices can be determined from the calculated $R_e(t)$ curve as $MTT=\int_0^\infty R_e(\tau) d\tau$, $BF=F_t$ and $BV=BF*MTT$. This approach can be implemented via a computer program for fast processing of perfusion maps by accounting for delay and dispersion without a time-consuming least-square-fitting process.

Alternatively, as the transport function $h(t)$ is simply a probability distribution function of the transit times, it is possible to use other functions such as a modified Gaussian function in equation (14) below to substitute equation (1) hence to describe $h_a(t)$ and $h_s(t)$ respectively.

$$h(t) = \begin{cases} \frac{1}{A} e^{-(t-t_0)^2/2\sigma^2} & (t \geq 0) \\ 0 & (t < 0) \end{cases} \quad (14)$$

Where $t_0 \geq 0$, $A=\sqrt{2\pi}\sigma[1+\text{erf}(t_0/\sqrt{2}\sigma)]/2$ and $$\text{erf}(t) \equiv \frac{2}{\sqrt{\pi}} \int_0^t e^{-x^2} dx$$

is the error function. Using the Gaussian function to substitute the first and second models in equations (3) and (8a) respectively, there are five parameters ($F_t$, $\sigma_2$, $t_2$, $\sigma_1$ and $t_1$) that need to be optimized through the fitting process.

Furthermore, the two models are not limited in scope to use in major vessel disease associated with the head of a patient, such as acute stroke or carotid artery stenosis. The models can be used in any intra-vascular application and therefore can apply to different parts of a patient's body, such as the cortex of the kidneys, lungs or spleen.

The models can be further extended to other cases where contrast may not totally remain intravascular but leak into the tissue, such as in a tumour. For a tissue ROI with a mean transit time of $\tau$, the tissue IRF can be described by the adiabatic approximation to the tissue homogeneity model as $$R(t, \tau) = \begin{cases} 1 & (t \leq \tau) \\ Ee^{-k(t-\tau)} & (t > \tau) \end{cases} \quad (15)$$

where the first term is the intravascular component and the second term is the leakage component. E is the extraction fraction of the tracer in the blood stream that leaks out of the vessel into tissue, and the tracer clearance rate constant $k=E*F_t/V_e$ is a rate constant at which the leaked contrast agent diffuses back into the blood stream and leaves the tissue, $V_e$ is the volume fraction of the extravascular and extracellular space (EES) in the tissue.

Normally there is perfusion heterogeneity associated with a distribution of transit time $\tau$ of blood vessels in tissue. Such a distribution can be described by a probability density function $h_s(\tau)$ such that the average tissue IRF involving leakage becomes $$R_s(t) = 1 - \int_0^t h_s(\tau) d\tau + Ee^{-kt} \int_0^t h_s(\tau) e^{k\tau} d\tau \quad (16)$$

where $h_s(\tau)$ can be described by the GVF model of equation (1) or by a Gaussian distribution function of equation (14).

The above described method for intravascular perfusion can be extended for perfusion measurements in a tumour by substituting equation (10) with (16) for the simulated $C_s(t)$ in equation (11). With two additional parameters, E and $V_e$ (or k), the method described above can be used to derive parameters for measuring both blood perfusion and permeability related indices including $F_t$, E and $V_e$. The parameters E and $V_e$ have a value between zero and one. The program selects certain starting values of E and V, such as $E=0.2$ and $V_e=0.4$, then further optimizes E and $V_e$ together with all other adjustable parameters (e.g. $F_t$, $\sigma_2$, $\alpha_1$, $\sigma_1$, $t_1$, $\alpha_2$, and $t_2$) using the least squares method of equation (12). The permeability surface area product can then be determined by $PS=-F_t \ln(1-E)$, where $PS=E*F_t$ when $E<<1$.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of estimating blood perfusion indices, for a region of interest (ROI) by operating a computer program on intensity data input to a computer comprising:
   a. providing a contrast agent to an artery, wherein said artery is upstream from a region of interest (ROI), wherein said ROI comprises tissue;
   b. measuring intensity data to provide a tissue contrast agent curve C(t) in said tissue, wherein said C(t) is a known intensity profile measured against time;
   c. measuring an arterial input function $AIF_a(t)$ in a vessel leading to said ROI, wherein said $AIF_a(t)$ is known intensity profile measured against time;
   d. estimating a tissue blood flow $F_t$ and a tissue impulse residue function R(t) by deconvolving $C(t)=(F_t/k_H)AIF_a(t) \otimes R(t)$, wherein $k_H=(1-H_a)/(1-H_t)$ is a correction constant using different values of an arterial hematocrit $H_a$ and a tissue hematocrit $H_t$, wherein said $H_a$ has a value of about 0.45, wherein said $H_t$ has a value of about 0.25, wherein when said $AIF_a(t)$ in a major artery comprises no delay and no dispersion, said C(t) can be derived by a convolution of said $AIF_a(t)$ and said R(t);
   e. determining a blood flow rate $F_t$ and a tissue impulse residue function $R_e(t)$ using said C(t) and a tissue input function $AIF_t(t)$ by deconvolving the relation $C(t)=(F_t/k_H)AIF_t(t) \otimes R_e(t)$, wherein $\otimes$ is the convolution operator, wherein said $AIF_t(t)$ comprises $AIF_t(t)=AIF_a(t) \otimes h_a(t)$, wherein $h_a(t)$ is a vascular transport function, wherein for $t<t_1$, $h_a(t)=0$ and for $$t \geq t_1, h_a(t) = \frac{1}{\sigma_1}e^{-(t-t_1)/\sigma_1},$$

wherein the initial value of a delay time $t_1$ can be determined by the maximum position of said R(t), wherein $\sigma_1=(t_1)(\beta_1)/(1-\beta_1)$, wherein $\beta_1$ is a known relative dispersion value having a range from 0 to 1;
   f. measuring an arterial input function $AIF_a(t)$ in said artery at a position that is upstream from said tissue;
   g. simulating a tissue contrast agent concentration curve $C_s(t)$ using a tissue transport function $h_s(t)$, wherein $$C_s(t) = (F_t/k_H)AIF_t(t) \otimes R_s(t) \text{ and } R_s(t) = 1 - \int_0^t h_s(\tau)d\tau,$$

wherein, said $$h_s(t) = \frac{1}{\sigma_2}e^{-(t-t_2)/\sigma_2}$$

for $t \geq t_2$, and said $h_s(t)=0$ for $t<t_2$, wherein t is time, wherein the initial value of a dispersion time $\sigma_2$ can be dertermined by 1/PH and the initial vaule of a minimum transit time $t_2$ can be determined by $MTT-\sigma_2$, wherein PH is a peak height and MTT is a mean transit time of a tissue transport function $h_e(t)$ in said tissue, wherein $h_e(t)$ is derived from said $R_e(t)$, wherein $h_e(t)=-dR_e(t)/dt$;
   h. using an iterative least squares method to fit the said simulated $C_s(t)$ to said measured tissue curve C(t) with four adjustable parameters ($F_t$, $t_1$, $t_2$ and $\sigma_2$);
   i. using a model-free deconvolution method to estimate starting values of said adjustable parameters for said iterative least squares fitting process in order to derive optimized values of said adjustable parameters; and
   j. calculating perfusion indices from the said optimized values of the adjustable parameters.

2. The method of claim 1, wherein said method further comprises using an adiabatic approximation to a homogeneity model in said tissue to provide an average tissue impulse residual function $R_s(t, t_3)$, wherein for $t \leq t_3$, said $R_s(t, t_3)=1$, wherein for $t>t_3$, said $R_{s(t, t3)}=Ee^{-k(t-t_3)}$, wherein t is time, wherein $t_3$ is an intravascular mean transit time, wherein E is an extraction fraction of said contrast agent in said blood that leaks out of a vessel into said tissue, wherein k is a clearance rate at which said contrast agent diffuses back into said blood and leaves said tissue, wherein said $k=E*F_t/V_e$, wherein said $V_e$ is a volume fraction of extravascular space and extracellular space in said tissue, wherein said E comprises a value between 0 and 1, wherein said $V_e$ comprises a value between 0 and 1;
   a. determining a simulated contrast agent curve $C_s(t)$, wherein said $C_s(t)$ is represented by $$C_s(t) = (F_t/k_H)AIF_t(t) \otimes R_s(t)$$

b. using an iterative least squares method to fit the said simulated $C_s(t)$ to said measured tissue curve C(t) with five adjustable parameters ($F_t$, $t_1$, $t_3$, E and $V_e$) in the situation where blood can leak out of a vessel.

3. The method of claim 1, wherein said intensity data is generated from a dynamic imaging scan of a contrast agent administered to a body, wherein said body lumen comprises an artery or a vein, wherein an image response from said contrast agent is recorded to computer data storage in a computer.

4. The method of claim 1, wherein said C(t) is a temporal concentration of said contrast agent obtained from said intensity data, wherein said intensity data comprises contrast images sequentially acquired from a region in a body, whereby said contrast agent concentration is plotted versus time.

5. The method of claim 1, wherein said $AIF_a$ is scaled upward according to a venous input function (VIF), wherein said VIF is based on a measured contrast intensity profile from a vein draining from said ROI.

* * * * *